US00PP15230P2

(12) United States Plant Patent
Olesen et al.

(10) Patent No.: US PP15,230 P2
(45) Date of Patent: Oct. 12, 2004

(54) ROSE PLANT NAMED 'POULTW002'

(50) Latin Name: *Rosa hybrida*
Varietal Denomination: POULtw002

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 32 days.

(21) Appl. No.: 10/738,160

(22) Filed: Dec. 16, 2003

(51) Int. Cl.[7] ..... A01H 5/00
(52) U.S. Cl. ..... Plt./108
(58) Field of Search ..... Plt./108

*Primary Examiner*—Anne Marie Grunberg
*Assistant Examiner*—Annette H Para

(57) ABSTRACT

A new garden rose plant of the shrub class which has abundant, deep pink flowers and attractive foliage. This new and distinct variety has shown to be uniform and stable in the resulting generations from asexual propagation.

2 Drawing Sheets

Botanical classification: *Rosa hybrida.*
Variety denomination: 'POULtw002'.

SUMMARY OF THE INVENTION

The present invention constitutes a new and distinct variety of garden rose plant which originated from a controlled crossing between a female parent plant named 'POULsint', non-patented, and a male parent plant, an unnamed seedling. The two parents were crossed during the summer of 1994 and the resulting seeds were planted in a controlled environment in Fredensborg, Denmark. The new variety is named 'POULtw002'.

The new variety may be distinguished from its female parent, 'POULsint', by the following combination of characteristics:

1. 'POULtw002' has an average growth height of 100 to 150 cm. 'POULsint' is low growing, 40 to 60 cm in height.
2. 'POULtw002' exhibits flowers with a larger diameter than those of 'POULsint'
3. 'POULtw002' develops flower buds in greater quantity per flowering stem that 'POULsint'.

The new variety may be distinguished from its unnamed pollen parent by the following combination of characteristics:

1. The pollen parent has a white flower color. The same of 'POULtw002' is Red-Purple Group 57A to 57B.
2. Open flowers of the pollen parent are 80 mm. The same of 'POULtw002' are 65 m.
3. Flowers are borne in clusters of 3 to 6 flower buds per stem on the pollen parent plant. 'POULtw002' bears flower buds in cluster of 7 buds per flowering stem.

The objective of the hybridization of this rose variety was to create a new and distinct variety for garden use with unique qualities, such as:

1. Uniform and abundant deep pink flowers;
2. Vigorous, but compact growth when propagated both as a budded rose and on its own roots;
3. Disease resistance;
4. Suitability for growth in a container.

This combination of qualities is not present in previously available commercial cultivars of this type, known to the inventors, and distinguish 'POULtw002' from all other varieties of which we are aware.

As part of their rose development program, L. Pernille Olesen and Mogens N. Olesen germinated the seeds from the aforementioned hybridization during winter of 1994 and conducted evaluations on the resulting seedlings in a controlled environment in Fredensborg, Denmark.

'POULtw002' was selected in the spring 1995 by the inventors as a single plant from the progeny of the aforementioned hybridization.

Asexual reproduction of 'POULtw002' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULtw002' are true to type and are transmitted from one generation to the next.

BRIEF DESCRIPTION OF THE DRAWINGS

The accompanying color illustration shows as true as is reasonably possible to obtain in color photographs of this type, the typical characteristics of the buds, flowers, leaves, and stems, of 'POULtw002'.

Specifically illustrated in SHEET 1:

FIG. 1.1; Open flower, stem showing cluster of open flowers, branching, and the attachment of leaves, and peduncles;

FIG. 1.2; Sepals, receptacle, and peduncle;

FIG. 1.3; Flower petals and petaloids, detached;

Specifically illustrated in SHEET 2:

FIG. 2.1; Flower bud closed, flower bud as sepals unfold, and partially open;

FIG. 2.2; Juvenile leaf exhibiting anthocyanin and mature leaf;

FIG. 2.3; Mature stem as well as juvenile stem exhibiting anythocyanin.

DETAILED DESCRIPTION OF THE VARIETY

The following is a description of 'POULtw002', as observed in its growth in a field nursery in Jackson County, Oreg. Observed plants are 3 years of age, grown on *Rosa*

*multiflora* understock. Color references are made using The Royal Horticultural Society (London, England) Colour Chart, 1995, except where common terms of color are used.

For a comparison, several physical characteristics of the rose variety 'POULor', a rose variety from the same inventors described and illustrated in U.S. Plant Pat. No. 12,511 dated Apr. 2, 2002, are compared to 'POULtw002' in Chart 1.

CHART 1

| | 'POULtw002' | 'POULor' |
|---|---|---|
| Bud color as sepals unfold | Red Group 45C. | Red-Purple Group 63B. |
| Plant Size | 100 to 150 cm (h) × 100 cm (w). | 70 cm (h) × 60 cm (w). |
| Flower diameter when fully open | 65 mm | 35 to 45 mm |

Parents:

*Female Seed Parent*.—'POULsint'.

*Male Pollen Parent*.—Unnamed seedling.

FLOWER AND FLOWER BUD

Blooming habit: Continuous.

Flower bud:

*Size*.—Upon opening, 20 mm in length from base of receptacle to end of bud.

*Bud form*.—Broad based to pointed ovoid.

*Bud color*.—As sepals unfold, petals are Red Group 45C. At ¼ opening petals are Red Group 53D.

*Sepals*.—Upper Surface: Color: Yellow-Green Group 144A to 144B. Anthocyanin: Greyed-Purple Group 183A. Surface: Slight pubescence observed. Lower Surface: Color: Yellow-Green Group 144A. Anthocyanin: Greyed-Purple Group 183A. Texture: Stipitate glands are in medium to abundant quantity. Sepal Shape: Sepal apex is cirrose. Base is flat at union with receptacle. Sepal Margin: Margins have strong foliaceous appendages on three of the five sepals. Size: 25 mm (l)×7 mm (w).

*Receptacle*.—Surface: Smooth to glabrous. Shape: Urn-shaped. Size: 6 mm (h)×7 mm (w). Color: Green Group 143B. Anthocyanic pigments the color of Greyed-Red Group 182C observed.

*Peduncle*.—Surface: Stipitate glands in medium quantity. Length: 30 mm average length. Color: Yellow-Green Group 145A. Anthocyanic pigments the color of Greyed-Red Group 181A observed. Strength: Somewhat strong.

*Borne*.—In clusters or cymes with 7 flowers per stem.

Flower bloom:

*Fragrance*.—Light floral scent.

*Duration*.—The blooms have a duration on the plant of approximately 10 to 14 days. Afterwards, petals fall cleanly away from plant.

*Size*.—Flower diameter is 65 mm when open.

*Form*.—General shape is a rosette with overlapping petals. Flowers open fully when mature, revealing reproductive organs.

*Shape of flower when viewed from the side*.—Upon opening, upper part: Flat. Upon opening, lower part: Concave. Open flower, upper part: Flat. Open flower, lower parts: Convex.

*Petalage*.—25 to 30 petals under normal conditions with 6 petaloids.

Color:

*Upon opening, petals*.—Outermost petals: Outer side: Red-Purple Group 57A to 58B. Inner Side: Red-Purple Group 57A. Innermost petals: Outer side: Red-Purple Group 61B. Inner Side: Red-Purple Group 57A.

*Upon opening, basal petal spots*.—Outermost petals: Outer side: White Group 155B. Inner Side: White Group 155B. Innermost petals: Outer side: White Group 155B. Inner Side: White Group 155B.

*After opening, petals*.—Outermost petals: Outer side: Red-Purple Group 57C. Inner Side: Red-Purple Group 57A. Innermost petals: Outer side: Red-Purple Group 57C. Inner Side: Red-Purple Group 57A.

*After opening, basal petal spots*.—Outermost petals: Outer Side: White Group 155A. Inner Side: White Group 155A. Innermost petals: Outer Side: White Group 155A. Inner Side: White Group 155A.

General tonality: On open flower Red-Purple Group 57A to 57B. No change in the general tonality at the end of the 10th day.

Petals:

*Petal Reflex*.—Strongly.

*Margin*.—Entire and uniform with point in center of margin. Medium to strong undulations of margin observed.

*Shape*.—Apex: Round. Base: Acute.

*Size*.—33 mm (1)×31 mm (w).

*Texture*.—Smooth.

*Thickness*.—Average.

*Arrangement*.—Not Formal.

Petaloids:

*Quantity*.—5 to 8.

*Color*.—Upper Surface: Red-Purple Group 57A. Lower Surface: Red-Purple Group 57C.

*Size*.—24 mm (1)×12 mm (w).

Reproductive organs:

*Pistils*.—Length: 7 mm. Quantity: 50 (actual count).

*Pollen*.—None observed.

*Anthers*.—Size: 2 mm in length. Color: Greyed-Yellow Group 161A. Quantity: 54 (actual count).

*Filaments*.—Color: Yellow-White Group 158A. Length: 4 mm.

*Stigmas*.—Superior in location to the length of the filaments and the height of the anthers. Color: Greyed-Yellow Group 162B.

*Styles*.—Color: Red-Purple Group 66A.

*Hips*.—None observed in the field nursery in Jackson County Oreg.

PLANT

Plant growth: Moderate, upright to bushy. When grown as a budded field grown plant on *Rosa multiflora* understock, the average height of the plant is 100 to 150 cm and the average width is 100 cm.

Stems:

*Color*.—Young wood: Greyed-Purple Group 187B to Yellow-Green Group 144B. Anthocyanin: Greyed-Purple Group 183B located on new shoots and leaves. Older wood: Smooth Thorns:

*Incidence*.—32 thorns per 10 cm of stem.

*Size*.—Average length: 8 mm.

*Color*.—Greyed-Purple Group 183B.

*Shape*.—Deeply Concave.

Plant foliage: Normal number of leaflets on normal leaves in middle of the stem: 5 to 7 leaflets.

*Compound leaf size.*—110 mm (l)×60 mm (w).

*Quantity*.—Average.

*Color*.—Mature Foliage: Upper surface is: Green Group 138A to Yellow-Green Group 144A. Lower surface is Yellow-Green Group 144A. Juvenile foliage: Upper surface is: Greyed-Purple Group 183A, with light intonations of Yellow-Green Group 152A. Lower surface is: Greyed-Purple Group 183A, with light intonations of Yellow-Green Group 152A. Anthocyanin: Location: Juvenile foliage and new shoots. Color: Greyed-Purple Group 183A.

Plant leaves and leaflets:

*Stipules*.—Size: 37 mm. Margins: Finely serrated with medium quantity of stipitate glands. Color: Yellow-Green Group 144A to Yellow-Green Group 147B. Anthocyanin: Color: Greyed-Purple Group 183A.

*Petiole*.—Length: 30 to 35 mm. Above: Color: Yellow-Green Group 144B. Anthocyanin: Greyed-Purple Group 183A. Underneath: Thorns present.

*Rachis*.—Length: 50 mm. Above: Color: Yellow-Green Group 144B. Anthocyanin: Greyed-Purple Group 183A. Underneath: Thorns present.

*Leaflet*.—Size: 42 to 45 mm (l)×32 to 40 mm (w). Edge: Serrated. Shape: Generally ovate to round. Base is rounded. Apex shape is cuspidate. Texture: Smooth. Thickness: Thick. Arrangement: Odd pinnate. Venation: Reticulate. Glossiness: Glossy.

Disease resistance: Above average resistance to mildew, rust, black spot, and Botrytis under normal growing conditions in Jackson County, Oreg.

Cold hardiness: The variety 'POULtw002' has been found to be cold tolerant to USDA Cold Hardiness Zone 6.

We claim:

1. A new and distinct variety of rose plant of the shrub rose class, substantially as herein illustrated and described as a distinct and novel rose variety due to its abundant deep pink flowers, disease resistance, and extended period of bloom.

* * * * *

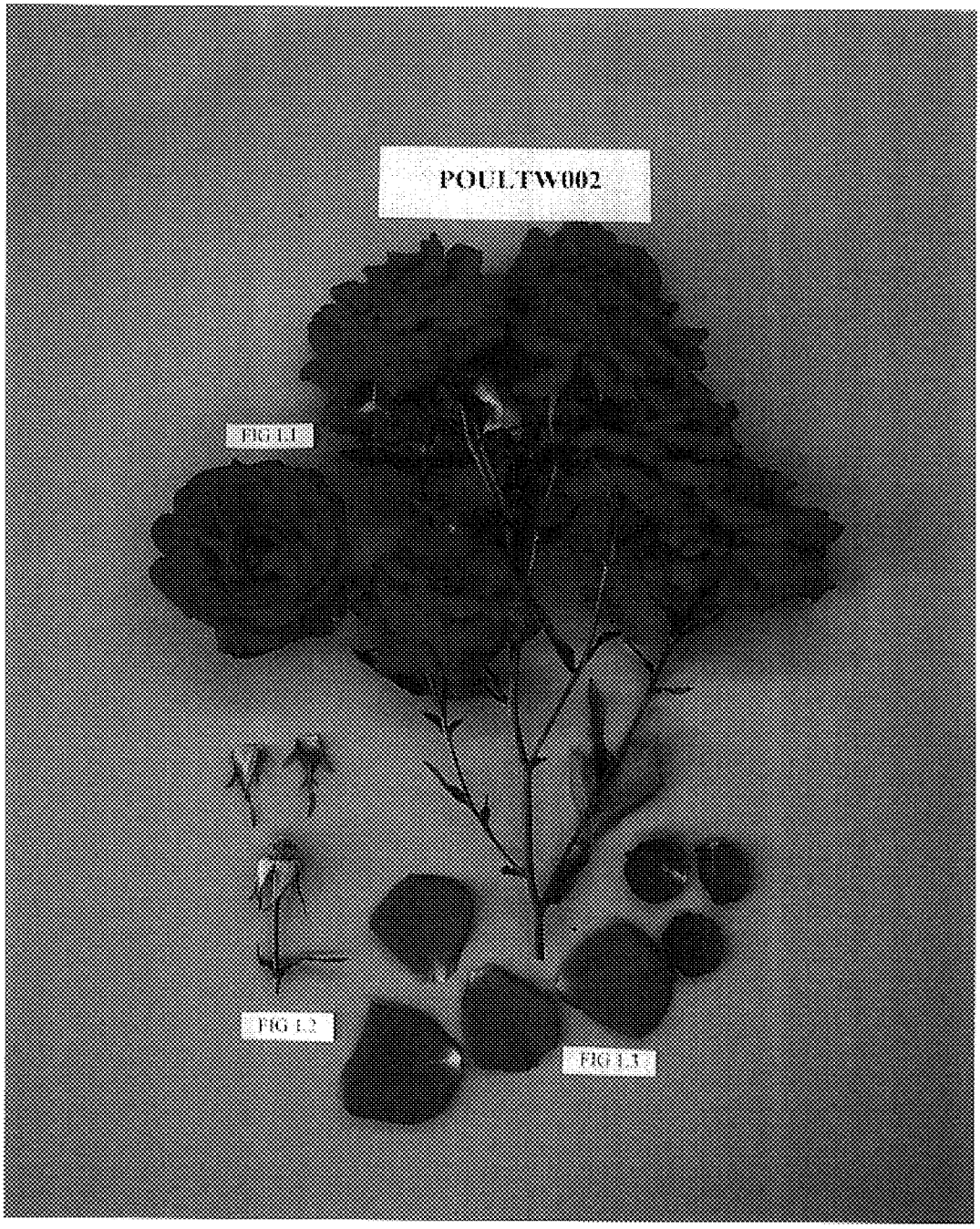
POULTW002
FIG 1.1
FIG 1.2
FIG 1.3

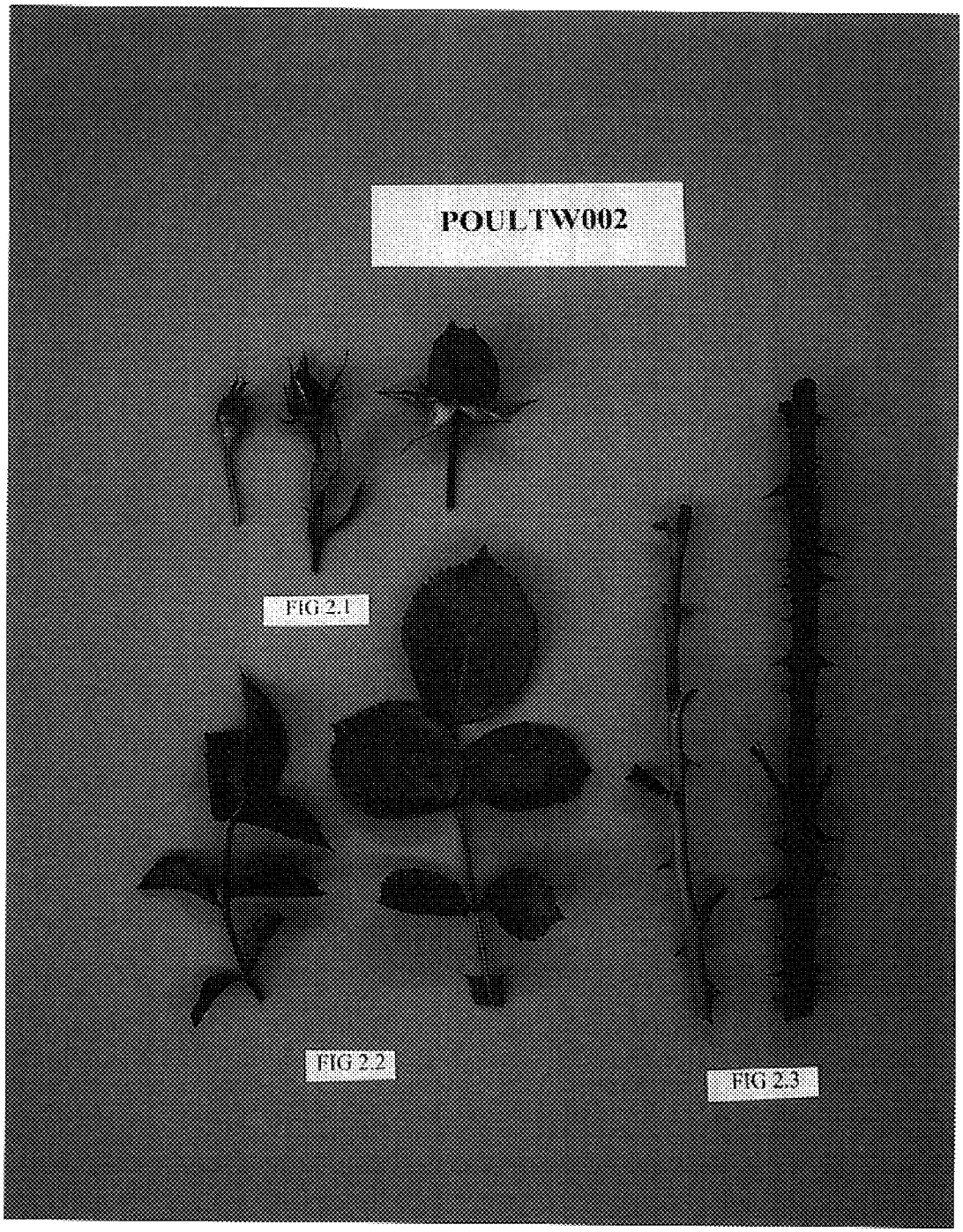
POULTW002
FIG 2.1
FIG 2.2
FIG 2.3